United States Patent
Kontos

(10) Patent No.: US 6,451,031 B1
(45) Date of Patent: Sep. 17, 2002

(54) BLOOD VESSEL SUTURING DEVICE WITH SINGLE GUIDE-WIRE/NEEDLE RECEIVING LUMEN

(75) Inventor: Stavros Kontos, Woodcliff Lake, NJ (US)

(73) Assignee: X-Site, L.L.C., Totowa, NJ (US)

( * ) Notice: Subject to any disclaimer, the term of this patent is extended or adjusted under 35 U.S.C. 154(b) by 0 days.

(21) Appl. No.: 09/532,972

(22) Filed: Mar. 21, 2000

(51) Int. Cl.[7] ............................................. A61B 17/04

(52) U.S. Cl. ..................................... 606/144; 606/145

(58) Field of Search .............................. 606/213, 139, 606/144, 145, 148

(56) References Cited

U.S. PATENT DOCUMENTS

| | | | |
|---|---|---|---|
| 3,807,407 A | 4/1974 | Schweizer | |
| 4,107,953 A | 8/1978 | Casillo | |
| 4,493,323 A | 1/1985 | Albright et al. | |
| 4,553,543 A | 11/1985 | Amarasinghe | |
| 4,757,827 A | 7/1988 | Buchbinder et al. | |
| 4,799,495 A | 1/1989 | Hawkins et al. | |
| 4,841,888 A | 6/1989 | Mills et al. | |
| 4,890,612 A | 1/1990 | Kensey | |
| 4,890,615 A | 1/1990 | Caspari et al. | |
| 5,037,433 A | 8/1991 | Wilk et al. | |
| 5,080,663 A | 1/1992 | Mills et al. | |
| 5,108,421 A | 4/1992 | Fowler | |
| 5,304,184 A | 4/1994 | Hathaway et al. | |
| 5,312,360 A | 5/1994 | Behl | |
| 5,312,423 A | 5/1994 | Rosenbluth et al. | |
| 5,320,632 A | 6/1994 | Heidmueller | |
| 5,324,306 A | 6/1994 | Makower | 606/144 |
| 5,336,229 A | 8/1994 | Noda | 606/139 |
| 5,336,231 A | 8/1994 | Adair | |
| 5,364,408 A | 11/1994 | Gordon | |
| 5,368,601 A | 11/1994 | Sauer et al. | |
| 5,374,275 A | 12/1994 | Bradley et al. | |
| 5,383,896 A | 1/1995 | Gershony et al. | |
| 5,387,221 A | 2/1995 | Bisgaard | |
| 5,391,182 A | 2/1995 | Chin | |
| 5,391,183 A | 2/1995 | Janzen et al. | 606/139 |
| 5,403,329 A | 4/1995 | Hinchcliffe | |
| 5,417,699 A | 5/1995 | Klein et al. | |
| 5,431,666 A | 7/1995 | Sauer et al. | |
| 5,437,631 A | 8/1995 | Janzen | 606/139 |
| 5,447,502 A | 9/1995 | Haaga | |
| 5,458,609 A | 10/1995 | Gordon et al. | |
| 5,474,543 A | 12/1995 | McKay | |
| 5,476,469 A | 12/1995 | Hathaway et al. | |
| 5,527,322 A | 6/1996 | Klein | 606/139 |
| 5,578,044 A | 11/1996 | Gordon et al. | |
| 5,613,974 A | 3/1997 | Andreas | |
| 5,676,689 A | 10/1997 | Kensey | |
| 5,700,273 A | 12/1997 | Buelna et al. | |
| 5,713,910 A | 2/1998 | Gordon et al. | |

(List continued on next page.)

FOREIGN PATENT DOCUMENTS

| | | |
|---|---|---|
| EP | 0 637 431 | 2/1995 |
| WO | 95/13021 | 5/1995 |

*Primary Examiner*—Gary Jackson
(74) *Attorney, Agent, or Firm*—Kenyon & Kenyon

(57) ABSTRACT

A device for sealing a tissue puncture including proximal and distal portions offset by a connecting member so that a needle may exit a lumen in the proximal portion through a needle insertion opening across a tissue receiving gap and enter through a needle receiving opening into a lumen in the distal portion. The distal lumen also has an opening for a guide wire. A method for sealing a tissue puncture by inserting a device such as that described above into the puncture via a guide wire, which is removed, so that the tissue is within the tissue receiving gap, and inserting a first suture needle distally from the proximal lumen, through the tissue, and into the distal lumen. The device is then rotated and a second suture needle similarly penetrates the tissue at a second location, and the device is withdrawn and the suture is tightened.

28 Claims, 9 Drawing Sheets

U.S. PATENT DOCUMENTS

| | | |
|---|---|---|
| 5,720,757 A | 2/1998 | Hathaway et al. |
| 5,728,133 A | 3/1998 | Kontos |
| 5,779,719 A | 7/1998 | Klein et al. |
| 5,792,152 A | 8/1998 | Klein et al. |
| 5,810,849 A | 9/1998 | Kontos |
| 5,810,850 A | 9/1998 | Hathaway et al. |
| 5,814,065 A | 9/1998 | Diaz |
| 5,820,631 A | 10/1998 | Nobles |
| 5,830,125 A | 11/1998 | Scribner et al. |
| 5,843,098 A | 12/1998 | Allen et al. |
| 5,846,253 A | 12/1998 | Buelna et al. |
| 5,855,585 A | 1/1999 | Kontos |
| 5,860,990 A | 1/1999 | Nobels et al. |
| 5,868,762 A | 2/1999 | Cragg |
| 5,876,411 A | 3/1999 | Kontos |
| 5,902,311 A | 5/1999 | Andreas et al. |
| 5,910,155 A | 6/1999 | Ratcliff et al. |
| 5,921,994 A | 7/1999 | Andreas et al. |
| 5,928,266 A | 7/1999 | Kontos |
| 6,036,699 A | 3/2000 | Andreas et al. |

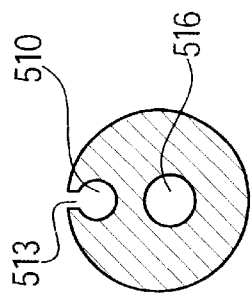
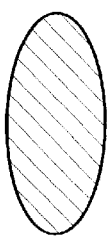
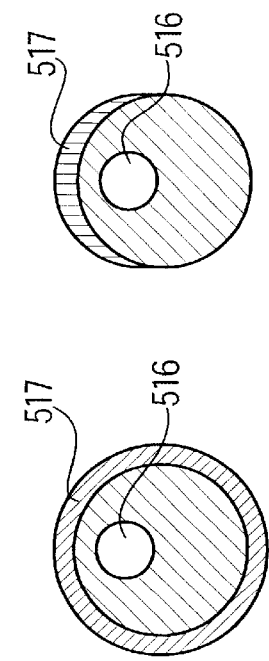
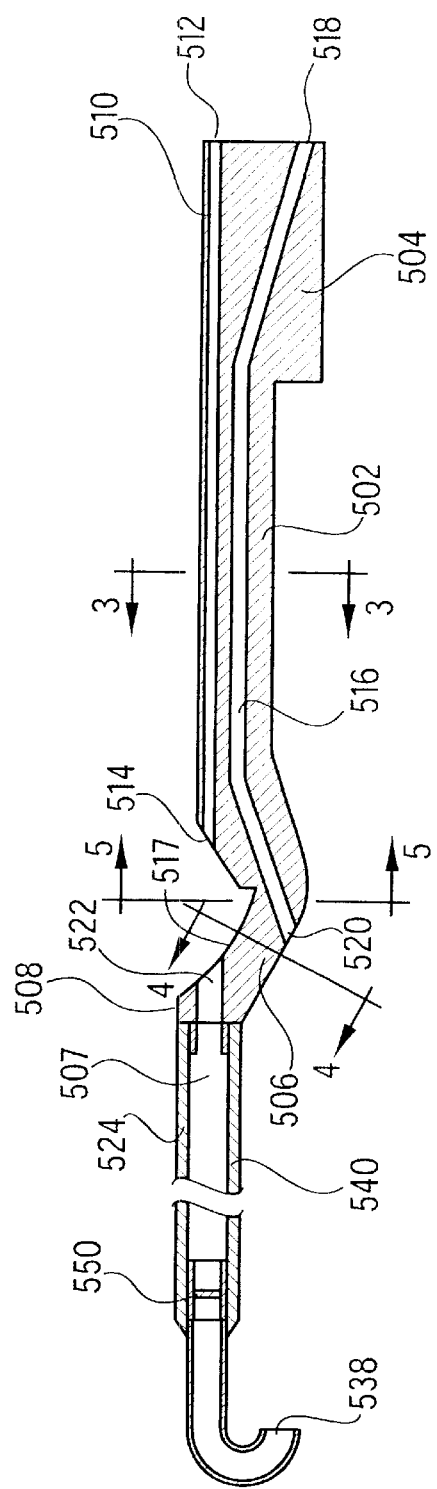

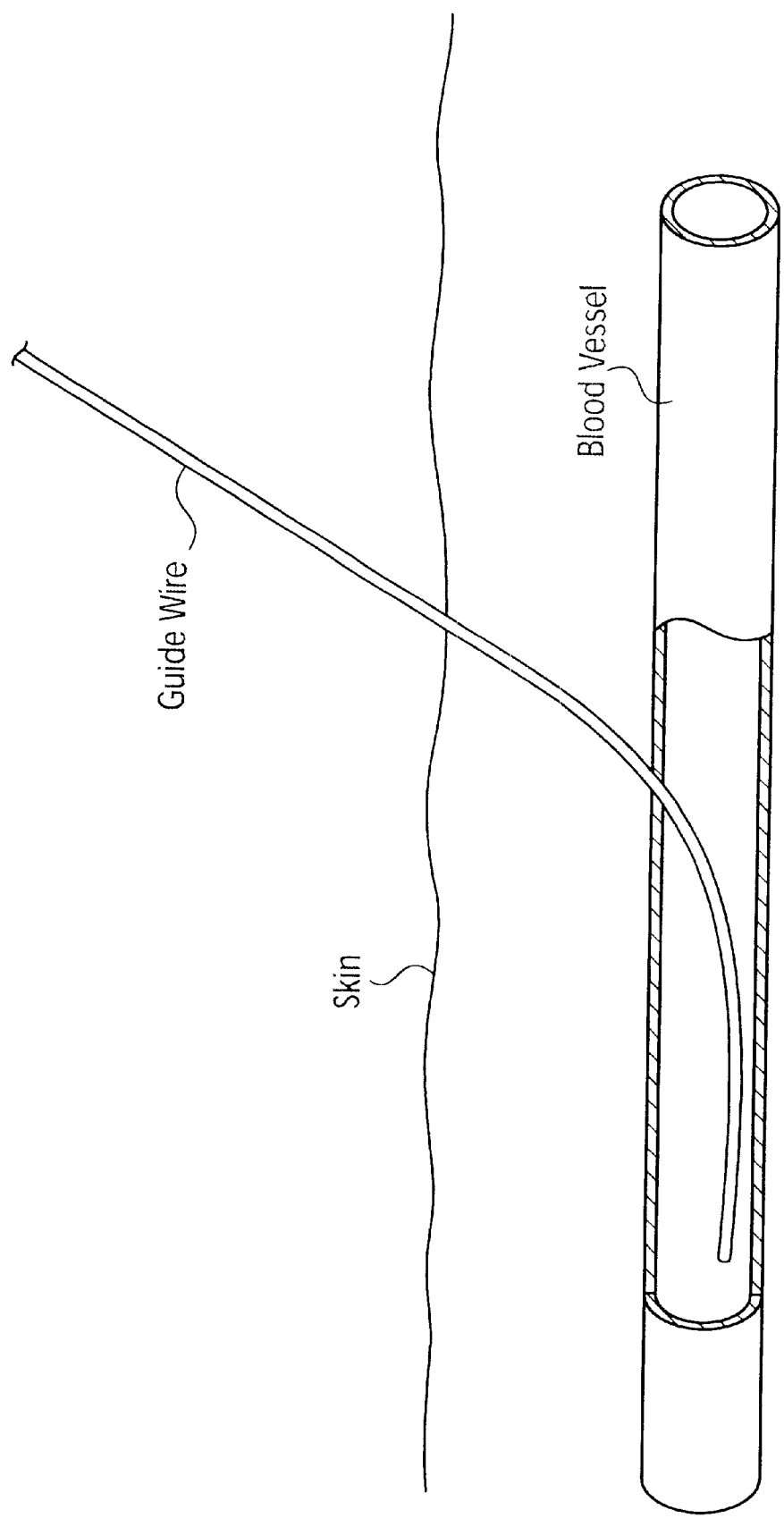

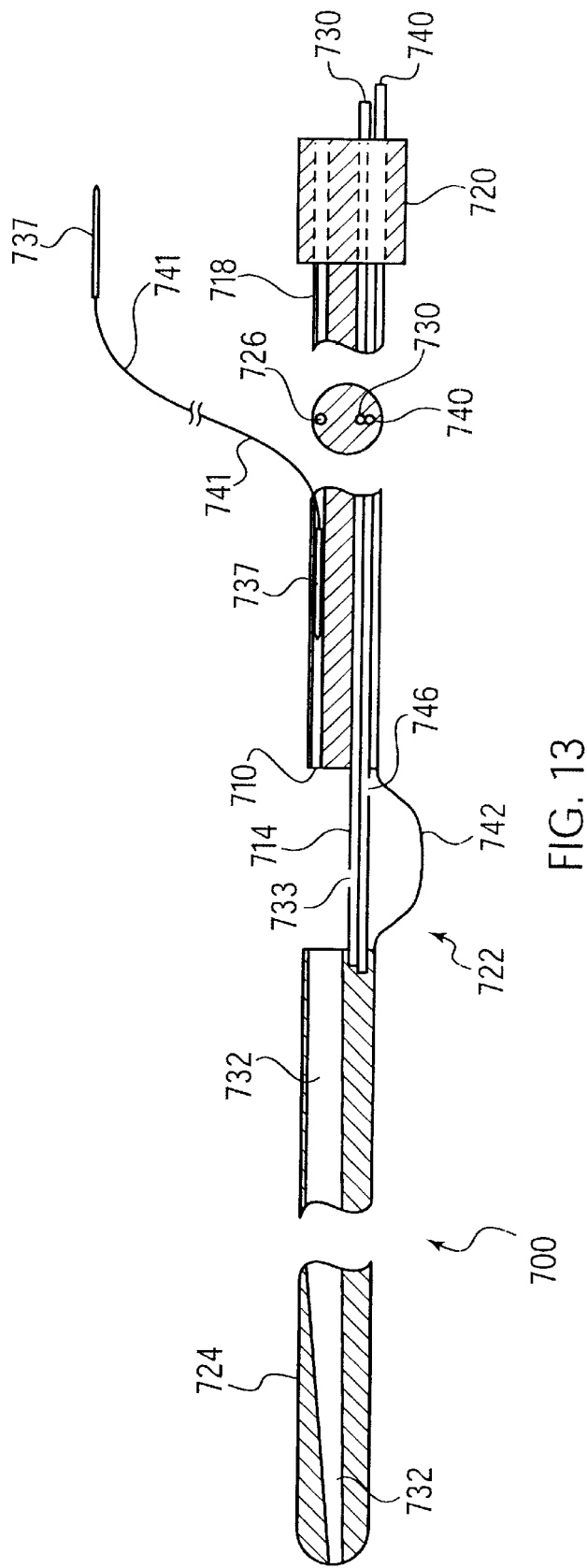
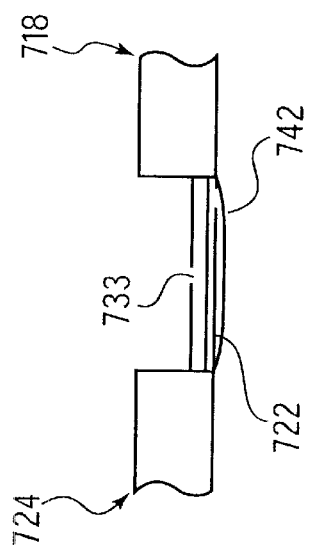
FIG. 13
FIG. 14

BLOOD VESSEL SUTURING DEVICE WITH SINGLE GUIDE-WIRE/NEEDLE RECEIVING LUMEN

FIELD OF THE INVENTION

The present invention relates generally to surgical instruments, and more specifically to devices for the suturing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument such as a catheter into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Such procedures also involve the insertion of a guide wire into the blood vessel tract to help guide tools to perform treatments at the target location. Of course, at the end of such a procedure, the opening in the wall of the blood vessel must be sealed to prevent bleeding while facilitating healing of the wound. This sealing has commonly been accomplished by the application of direct pressure over the puncture site by a physician or other trained medical professional. However, this technique is time consuming and may lead to complications such as thrombosis, which may be dangerous to the patient.

Other sealing techniques include the application of a sealing member or plug of material (most often biogenic sealing material) over the opening in the blood vessel to seal the wound. However, proper placement of sealing members and plugs is difficult to achieve and materials left inside the body may pose serious health risks to the patient if, for example, the material enters the blood stream.

SUMMARY OF THE INVENTION

The present invention is directed to a device for sealing a puncture in an anatomical structure, the device comprising a proximal portion having a needle insertion lumen extending therethrough to a needle insertion opening, a distal portion including a needle receiving opening facing the needle insertion opening across a tissue receiving gap and opening into a distal lumen and a connecting portion coupled between the proximal and distal portions and offset from the proximal and distal portions to create the tissue receiving gap whereby, when the connecting portion is received within a puncture in an anatomical structure, a portion of the anatomical structure received within the tissue receiving gap is located between the needle insertion opening and the needle receiving opening.

The distal lumen extends from the needle receiving opening to a guide wire opening located distally in the distal portion of the device. The distal lumen is sized to accommodate a guide wire, such as would be typically used during vascular procedures.

The device can be inserted into the puncture by slipping the proximal end of the guide wire into the guide wire opening of the device, through the distal lumen, and out of the needle receiving opening. The device may then be slid along the guide wire. The guide wire can then be removed so that the device can be placed in the desired position in the puncture and the suturing procedure can begin, upon removal of the guide wire, the distal lumen will have room to receive the suturing needles.

Running the guide wire coaxially through the distal lumen of the device helps to avoid over-dilation of the puncture by eliminating the need for a side-by-side arrangement of the device and guide wire through the puncture. The distal lumen is also useful for reinserting the guide wire through the puncture, if such reinsertion becomes necessary. This arrangement also allows the distal portion of the device to be shorter, since it is not necessary to include separate lumens for capturing the suturing needles and for guiding the device along the guide wire.

In addition, the present invention is directed to a method for sealing a puncture in an anatomical structure including the steps of inserting into the puncture a device having a needle insertion opening and a needle receiving opening separated by a tissue receiving gap and positioning the device so that the needle insertion opening is located on a proximal side of the anatomical structure and the needle receiving opening is located on a distal side of the anatomical structure with a first portion of the anatomical structure received within the tissue receiving gap. At the suturing stage of a medical procedure, a guide wire will often still be running through the puncture into the anatomical structure. Insertion of the device can be accomplished by inserting the proximal end of guide wire into the guide wire opening and sliding the guide wire through the distal lumen until the device is in the desired position. The guide wire is then removed from the distal lumen through the needle receiving opening before the arch section enters the skin line and before inserting suturing needles.

A first needle coupled to a first portion of suture is inserted distally through the needle lumen to exit the device via the needle insertion opening, penetrate the first portion of the anatomical structure and re-enter the device via the distal lumen and the device is rotated so that a second portion of the anatomical structure is located within the tissue receiving gap between the needle insertion opening and needle receiving opening. Then a second needle coupled to a second portion of suture is inserted distally through the needle lumen to exit the device via the needle insertion opening, penetrate the second portion of the anatomical structure and re-enter the device via the distal lumen. The device is withdrawn from the anatomical structure and the first and second portions of suture are tightened to draw the sides of the puncture together.

BRIEF DESCRIPTION OF THE DRAWINGS

FIG. 2 shows a cross-sectional side view of the device of FIG. 1;

FIG. 3 shows a cross-sectional view of the device of FIG. 2 taken along line 3—3 of FIG. 2;

FIG. 4 shows a cross-sectional view of the device of FIG. 2 taken along line 4—4 of FIG. 2;

FIG. 5 shows a cross-sectional view of the device of FIG. 2 taken along line 5—5 of FIG. 2;

FIG. 5A shows an alternative cross-sectional view of the device of FIG. 2 taken along line 5—5 of FIG. 2;

FIG. 8 shows a partially cross-sectioned side view of a guide wire in an initial position within a blood vessel;

FIG. 13 shows a side view of a cross-section of a suturing device according to a further embodiment of the invention with an expandable member; and FIG. 14 shows the suturing device of FIG. 13 before entering the blood vessel with an expandable member in a deflated state.

DETAILED DESCRIPTION OF THE INVENTION

Figure 1:
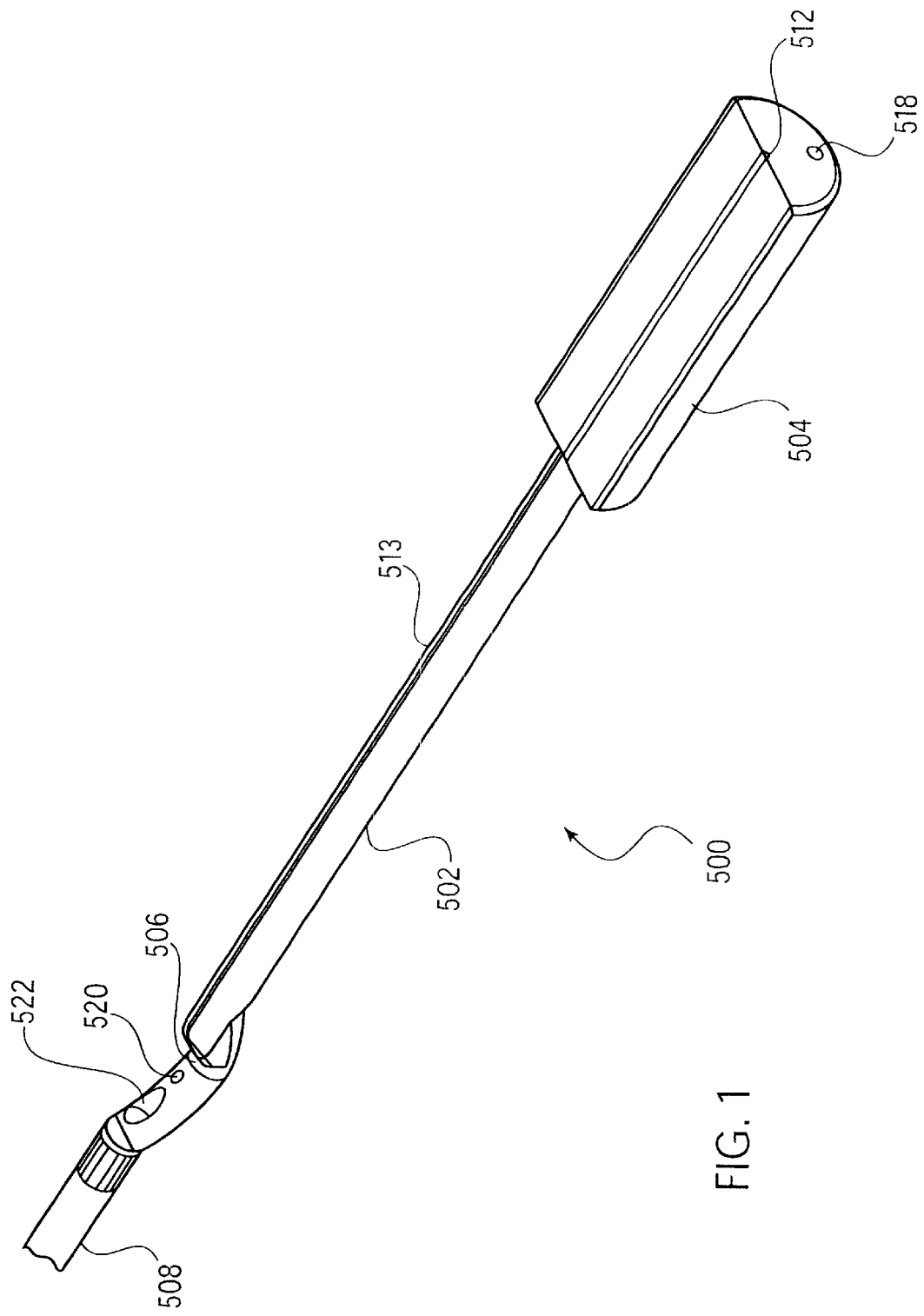
FIG. 1 shows a perspective view of an exemplary embodiment of a suturing device according to the present invention.

FIG. 1 shows a device 500 according to a preferred embodiment of the invention including a tube 502 having a distal section of substantially circular cross-section, and a handle 504 at a proximal end thereof. A central part 506 which is coupled to a distal end of the proximal part 502, curves away from an axis of the proximal part 502 along an arc by which the central part 506 returns toward the axis of the proximal part 502 to connect with a distal part 508. The central arcuate portion may preferably be substantially circular with a radius of from 0.100" to 0.600". Thus, a distal end of the proximal part 502 faces a proximal end of the distal part 508 across a tissue receiving gap formed by the central part 506. A cross-sectional area of the central part 506 is substantially equal to that of the distal part 508 and the cross-sectional areas of both the central part 506 and the distal part 508 remain substantially constant along their entire lengths while a cross-sectional area of the proximal part 502 may preferably be equal or slightly greater than that of the distal part 508 and the central part 506. More specifically, it is preferable that a maximum outer diameter of the distal part 508 be no larger than a maximum outer diameter of the central part 506. In this way, the opening in the blood vessel is not further stretched by the introduction of the distal part therethrough.

The cross sectional side view of FIG. 2 shows further features of the preferred embodiment. A needle insertion lumen 510 extends through the proximal part 502 and the handle 504 from a needle insertion opening 512 formed in a proximal end of the handle 504 to an opening 514 formed at a distal end of the proximal part 502. A suture removal slot 513 extends through the surface of the handle 504 and the tube 502 to open an interior of the needle insertion lumen 510 to the outside of the device 500 along an entire length of the needle insertion lumen 510. A width of the suture removal slot is less than a diameter of the needle insertion lumen 510 so that needles received therein may not escape via the suture removal slot 513.

A position indication lumen 516 extends from an opening 518 formed in the handle 504 through a portion of the central part 506 to openings 520 formed in the central part 506. A needle receiving opening 522 formed in the proximal end of the distal part 508 extends into a distal lumen 507 which extends axially through the distal part 508. The distal lumen 507 extends for a length more than twice the length of needles 526 which are to be used with the device.

In an initial configuration, no needles are received within the device 500. Alternatively, all or a portion of a first needle 526 may be received within the needle insertion lumen 510 so long as the pointed distal end of the first needle 526 remains within the needle insertion lumen 510.

The device is preferably substantially rigid from the proximal end of the handle 504 to the needle entry opening 522 at the proximal end of the part 508 with a flexible tube extending distally from the distal end of the part 508. This rigid structure ensures that the openings 514 and 522 remain properly aligned with one another during the procedure.

A distal lumen 507 extends through the distal part 508 from the needle receiving opening 507 to the guide wire opening 538.

FIG. 4 shows a preferred embodiment of the invention where the arcuate portion of central part 506 has an oval cross section. The oval cross section allows the arcuate structure to be thinner in a first direction with respect to the tissue receiving gap so that the tissue receiving gap can be deeper and a larger portion of the blood vessel wall extends between the openings and the points of penetration of the needles. By accepting more of the blood vessel wall, the device can make a more stable and secure suture, further from the edge of the puncture.

FIG. 5 also shows another preferred embodiment, wherein the rigid arcuate member of central part 506 includes a raised ridge 517 serving as a catch, or stop, to assist in accurate placement of the device. In the preferred embodiment, the raised ridge 517 is located on a proximal side of the central part 506 so that when the device is inserted into a puncture in a blood vessel the edge of the puncture will catch on the ridge when the device has reached the appropriate depth. The ridge may be formed inside the concave portion of the central part 506, as depicted in FIG. 5 or the ridge may be formed around the entire circumference as shown in FIG. 5A.

The distal part 540 is primarily made as a flexible tube 524 which may, e.g., preferably be constructed of a thermoplastic such as polyurethane, polyethylene, or the like, in two or three parts bonded together. The various parts of the flexible tube 524 may preferably be either extruded or molded. Those skilled in the art will recognize that it may be more economical to extrude the parts including lumens, while the more complex, and curved sections of the rigid section 502 may be molded. The length of the device may be selected to fit the requirements of a particular situation and is preferably between 1" and 16" in length. The flexibility of the distal part 540 allows the distal part 540 to bend and follow the direction of the blood vessel without straining the blood vessel.

Specifically, the distal part 540 of the device 1" is constructed so that it has enhanced flexibility relative to the proximal parts 502-504-508. In a preferred embodiment, as shown in FIG. 2, a distal end of the flexible tube 540 of distal part 508 may be biased so that, when in an unstressed state, it is "J" shaped—that is, the distal portion of flexible tube 524 is curved so that the guide wire opening 538 faces proximally. This facilitates insertion of the device 500 so that it contacts an inner wall of the blood vessel without damaging it. Specifically, the flexibility and "J" shape of the flexible tube 524 allows it to deflect away from the blood vessel's lining without penetrating or damaging the lining. Of course, when received on the guide wire, the "J" shape of the flexible tube 524 will be less pronounced. However, the bias will maintain a slight curvature of the flexible tube 524 deflecting the impact of the device 1" from the inside lining of the blood vessel.

The flexible tube 524 may also, however, be formed as a straight member or any other shape, as dictated by the shape of the anatomical structure and surrounding tissues.

In a preferred embodiment, distal lumen 507, contains a valve 550 to prevent blood from flowing through the distal lumen 507 during insertion of the device into the puncture. Without a valve to prevent the flow of blood through the distal lumen 507 it is possible that blood might escape through the distal lumen 507 while the device is being inserted into a blood vessel. Such excess blood could cause an undesirable condition such as hematoma. In the preferred embodiment, the valve should be positioned in a distal part of the distal lumen 507 so as to not inhibit the ability of the distal lumen 507 to receive suturing needles 526.

Figure 7:
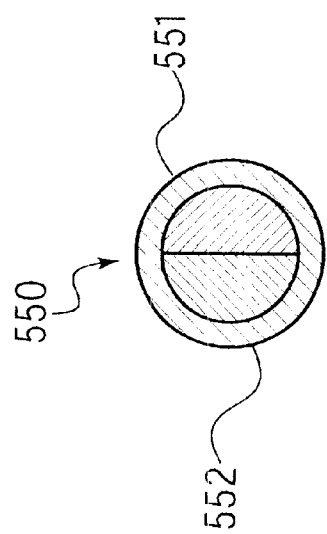
FIG. 7 shows a cross sectional end view, taken along line 7—7 of FIG. 6, of a preferred embodiment of a valve for placement in a distal lumen.
Figure 6:
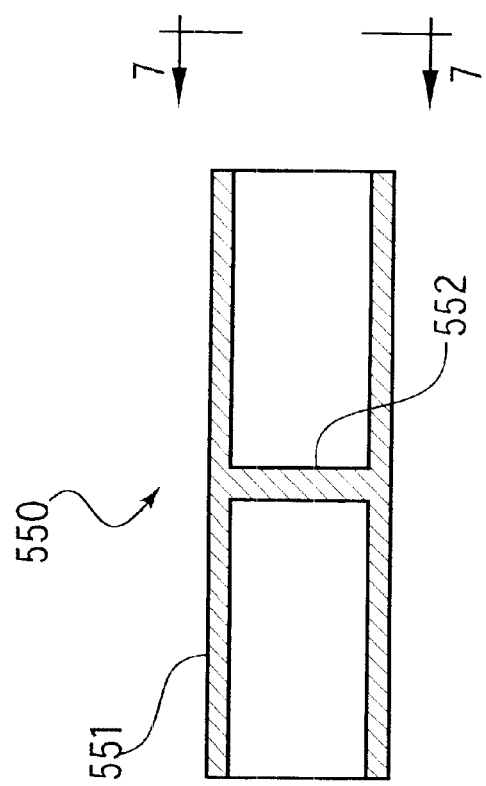
FIG. 6 shows a cross sectional side view of a preferred embodiment of a valve for placement in a distal lumen.

As depicted in FIGS. 6 and 7, a preferred embodiment of valve 550 includes a portion of a cylindrical tube 551, which may be made, for example, of a flexible material such as polyurethane or silicone. The tube 551 is placed coaxially in the distal lumen 507. The valve 550 also includes a slitted diaphragm 552, which may also be constructed of flexible material, situated in the interior cross section of the cylindrical tube 551. The tension of the material comprising the slitted diaphragm 522 will substantially prevent blood from flowing through the slit. However, the slitted diaphragm 522 is flexible enough to allow a guide wire to be pushed through during insertion of the device 500 into a blood vessel.

This device may preferably be used to close punctures of 9.0 French size and smaller (each French size representing 0.13" in diameter). The flexible tube 524 of the distal portion will, therefore, preferably be 9.0 or smaller. As described below in reference to further embodiments of the invention, devices employing two or more pairs of needles 526 may be employed to close punctures larger than 9.0 French size. Each of the needles 526 may preferably be constructed of nitenol material, be between ½" and 8" in length and have a diameter between 0.010" and 0.030".

In operation, as shown in FIG. 8, when an invasive procedure has been performed on a patient and a catheter previously inserted into a blood vessel (or other structure within the body) has been withdrawn, a guide wire may be left in place extending through the tissue tract, through the puncture into the blood vessel. The puncture must now be sealed.

Figure 9:
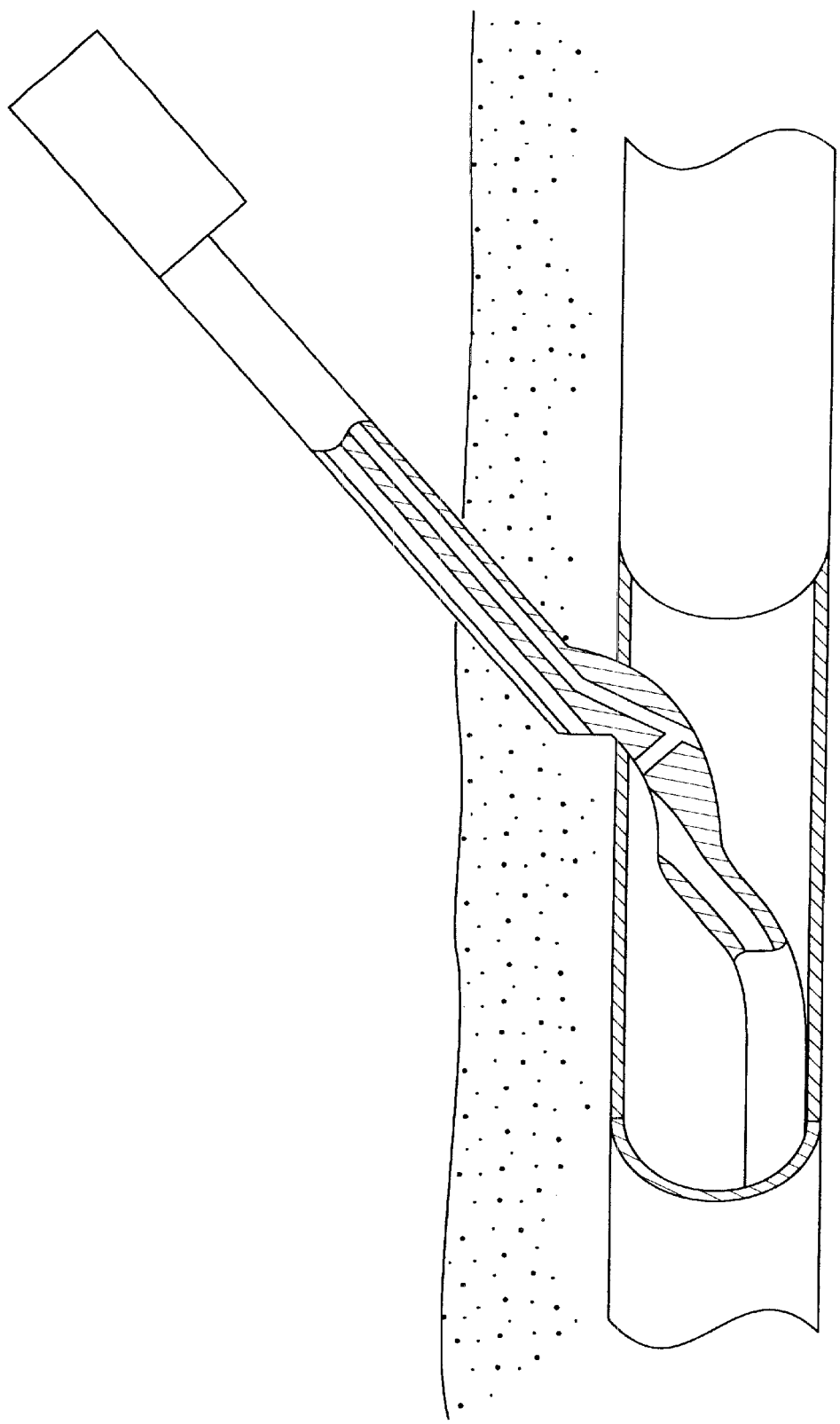
FIG. 9 shows a partially cross sectional side view of a the device of FIG. 1 inserted into a blood vessel via a guide wire.

A proximal end of the guide wire may be inserted through the distal lumen 507 and the device 500 is inserted into the body and moved along the guide wire through the puncture as depicted in FIG. 9. During the insertion and placement of the device 500, valve 550 in the distal lumen 507 substantially prevents blood from unnecessarily flowing from the blood vessel, through the distal lumen 507, and onto the patient's wound. The guide wire is withdrawn as the arch section is entering into the skin line.

By observing the position indication lumen 516 and the needle insertion lumen 510, the doctor may determine when the device 500 is in the desired position. Specifically, when the device 500 is inserted far enough into the blood vessel, blood will be observed in the position indication lumen 516. However, if blood is observed in the needle insertion lumen 510, the doctor knows that the device 500 has been inserted too far into the blood vessel. When properly positioned within the blood vessel, the device 500 may be rotated to a specific orientation (if desired).

Figure 10:
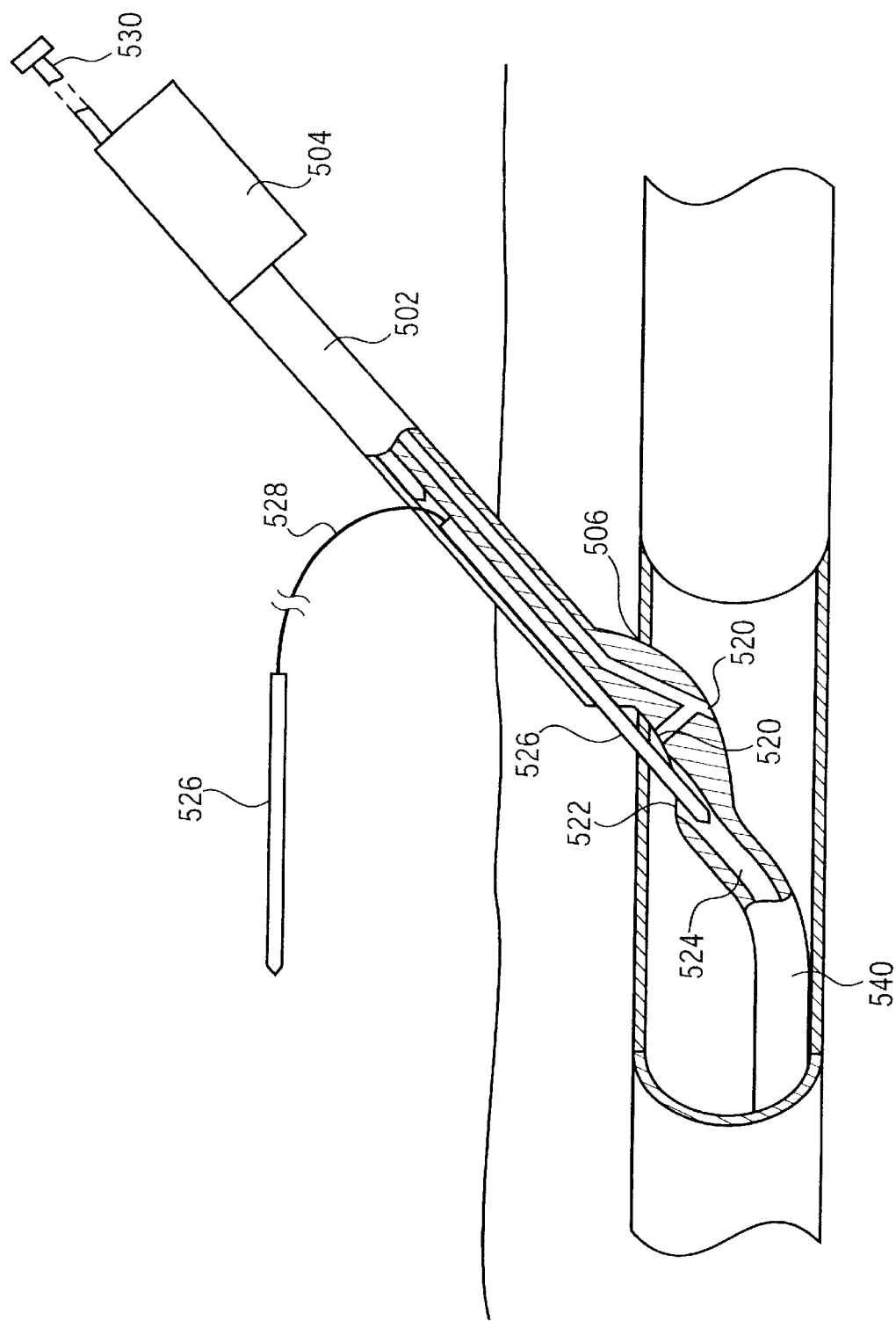
FIG. 10 shows a partially cross-sectional side view of the device of FIG. 1 in a first position for suturing a blood vessel.

As depicted in FIG. 10, with the device 500 properly positioned for the insertion of the first needle 526, the doctor inserts the first needle 526 and a first end of the loop of suture 528 attached thereto into the needle insertion lumen 510 through the opening 512 and pushes the needle 526 the suture 528 distally along the needle insertion lumen using the needle pusher 530. As the needle 526 is advanced distally, the sharpened distal end of the needle 526 exits the needle exit opening 514, penetrates the blood vessel wall and enters the distal lumen 507 via the needle receiving opening 522. The doctor continues to advance the needle 526 distally until the proximal end of the needle 526 is completely received within the distal lumen 507 and then withdraws the needle pusher 530 from the device 500.

Figure 11:
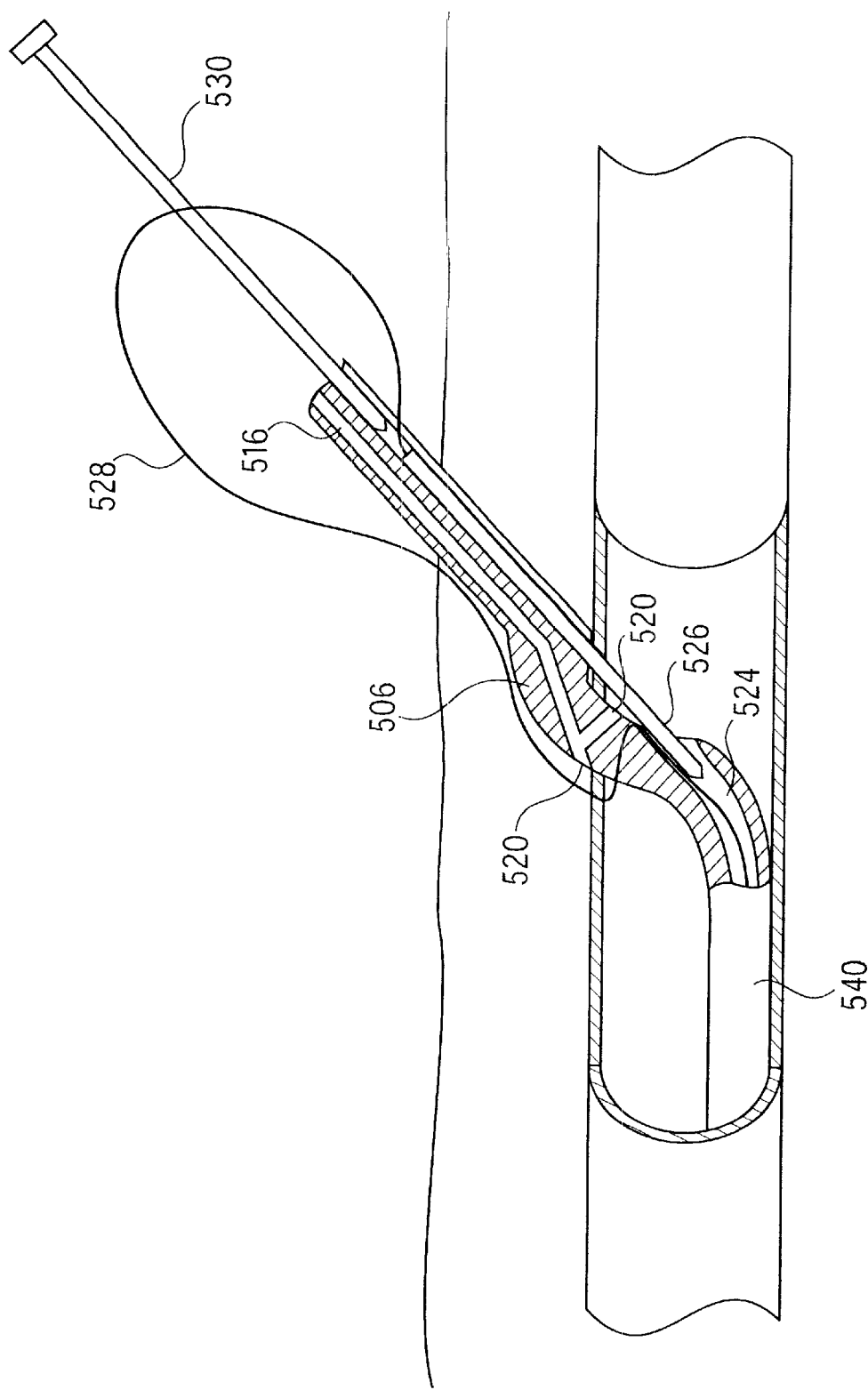
FIG. 11 shows a partially cross-sectional side view of the device of FIG. 1 in a second position for suturing a blood vessel.

Thereafter, the doctor rotates the device 500 to a second orientation while observing the position indication lumen 516 and the needle insertion lumen 510 to ensure that the blood vessel wall is still received between the opening 514 and the needle entry opening 522 as shown in FIG. 11. The second portion of the blood vessel wall received between the opening 514 and the needle entry opening 522 will usually be separated from the point at which the first needle 526 penetrated the blood vessel wall by approximately 180°. of course, those skilled in the art will understand that any angular separation may be achieved depending, for example, on the number of sutures the doctor wishes to use in sealing the blood vessel. When the device 500 is in the second orientation, the doctor inserts a second needle 526 and a second end of the loop of suture 528 coupled thereto into the needle insertion lumen 510 via the opening 512 and uses the needle pusher 530 to advance the second needle 526 distally through the needle insertion channel 510 and through the blood vessel wall until the proximal end of the second needle 526 is completely received within the distal lumen 507, as was done with the first needle 526.

Figure 12:
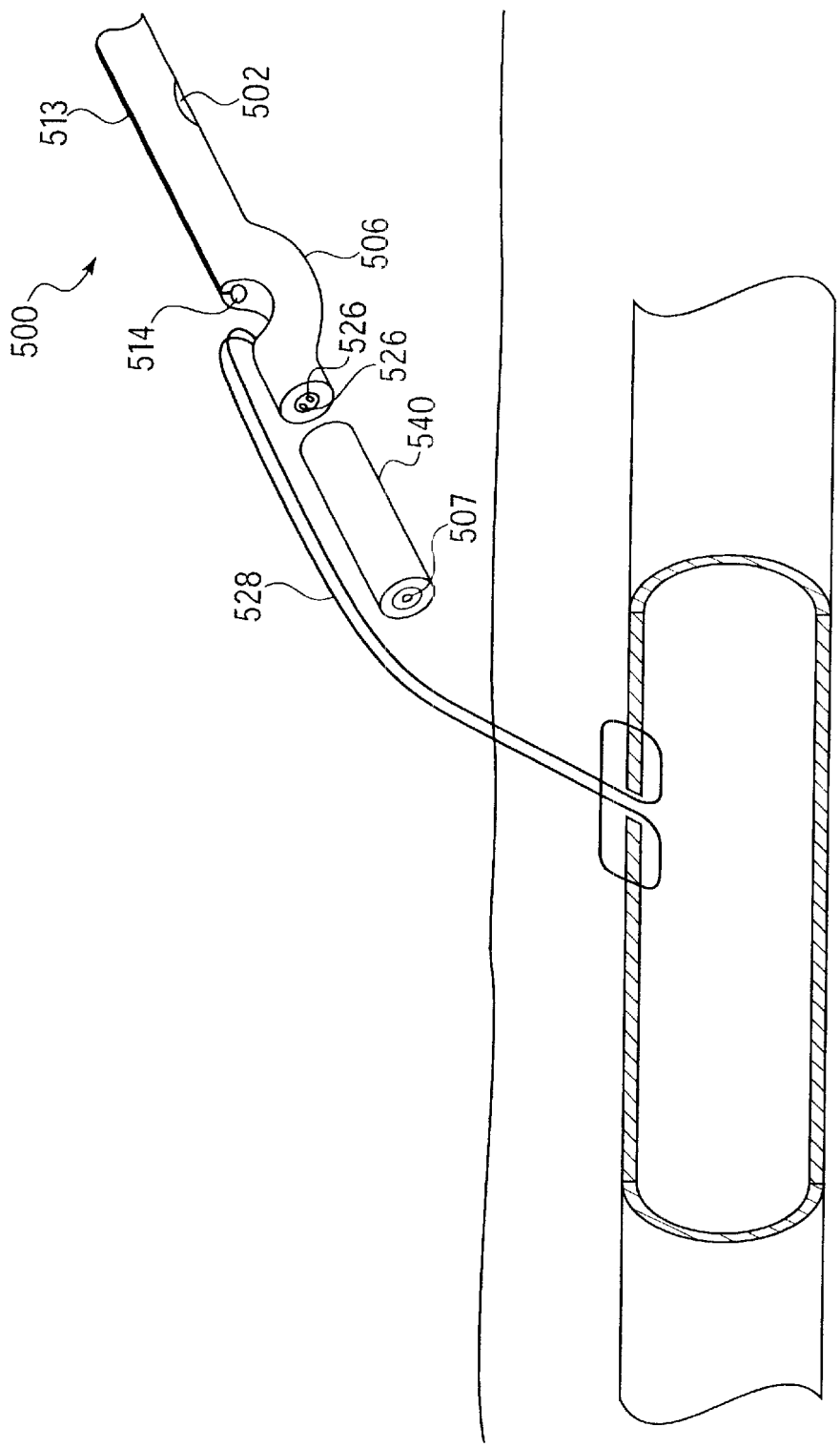
FIG. 12 shows a partially cross-sectional perspective view of the device of FIG. 1 after removal from the blood vessel.

As shown in FIG. 12, the doctor withdraws the needle pusher 530 from the device 500 and then withdraws the device 500 from the body, with the needles 526 received in the distal part 540. The doctor then cuts the suture from the needles and tightens and knots the suture loop 528 to seal the puncture.

The suture 528, which will preferably be in the range of 0.004" to 0.010" in diameter and from 15" to 35" in length, may be formed of either "reabsorbable" or "non-reabsorbable" material, as is well known in the art.

Those skilled in the art will understand that, for larger punctures, the device 500 may be used to insert as many sutures 528 as are required to seal the puncture. Specifically, in order to close punctures larger than size 9.0 French, a single suture 528 may not be sufficient. Therefore, instead of using the device 1" as described above to insert two sutures 528 approximately 180° apart, a doctor may, for example, insert four sutures 528 at 90° intervals using the technique described above. Then, when the device 1" has been withdrawn from the body, the doctor must knot together a first pair of sutures 528 which are separated by approximately 180° and then knot the second pair. The two pairs of sutures 528 may be distinguished by color coding or any similar technique.

FIGS. 13 and 14 illustrate a device 700 according to an additional embodiment of the present invention. The construction and operation of the device 700 is substantially similar to that of the device 500 of FIGS. 1–12, except for the construction of the central portion 722, the flashback lumen 730 and an additional inflation tube 740, as described below.

Specifically, the central portion 722 is located within a gap 714 situated between the proximal and distal parts 718 and 724. The central portion 722 includes an expandable member 742, preferably a balloon, which is adapted to be inflated via the inflation tube 740, which extends from the proximal end of the proximal part 718 to an inflation opening 746 formed at the distal end of the proximal portion 718. When air or other fluid is supplied to the expandable member 742 via inflation tube 740, the expandable member 742 expands away from a surface of the central portion 722 opposite the gap 714 to press against the wall of the blood vessel. This pushes the device 700 toward a portion of the blood vessel wall opposite the expandable member 742 so that this portion of the blood vessel wall is received at a predetermined location, preferably deep, within the gap 714.

In operation, when the device 700 is inserted into a blood vessel of a patient, the expandable member 742 is initially in a deflated state, extending along a surface of the device 700 adjacent to the flashback lumen 730 (see FIG. 13). When the device 700 is positioned so that the opening 733 is on a distal side of the puncture, and the opening 710 is positioned on the proximal side of the puncture, the physician provides a gas or a liquid through the inflation tube 740 to expand the expandable member 742. The expandable member 742 contacts a first portion of the blood vessel wall to aid in positioning the openings 733 and 710 of the device 700 at a first desired penetration location on the blood vessel wall. The expandable member 742 thus is used to prevent blood leakage during the sealing procedure by occluding the opening in the blood vessel wall. Thereafter, the user inserts a first needle 737 distally through the needle insertion lumen 726, as described above, to pierce the wall of the blood vessel at the first desired location, and enter the distal lumen channel 732 drawing a first end of a loop of suture 741 therethrough. The first needle 737 is pushed distally until the entire first needle 737 is completely received within the distal lumen 732.

The user then rotates the device 700 to a second position within the puncture. Thereafter, the user inserts a second needle 737, and a second end of the length of suture 741, through a second desired penetration location on the blood vessel wall until the entire second needle 737 is received within the distal lumen 732 and deflates the expandable member 742. The device 700 is then removed from the patient's body and the two ends of the loop of suture 741 are coupled together to seal the opening.

Those skilled in the art will understand that, as the needles of this device penetrate tissue on only one side of the puncture at a time, the diameter of the proximal part may be made as small as that of the distal and central parts and the puncture need not be further stretched as is required in larger diameter devices that deploy needles simultaneously to opposite sides of the puncture.

There are many other variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

What is claimed is:

1. A device for sealing a puncture in an anatomical structure comprising:
   a proximal portion having a needle insertion lumen extending therethrough to a needle insertion opening;
   a distal portion including a needle receiving opening facing the needle insertion opening across a tissue receiving gap and opening into a distal lumen, the distal lumen extending from the needle receiving opening to a distal guide wire opening; and
   a connecting member coupled between the proximal and distal portions and offset from the proximal and distal portions to create the tissue receiving gap whereby, when the connecting member is received within a puncture in an anatomical structure, a portion of the anatomical structure received within the tissue receiving gap is located between the needle receiving opening and the needle insertion opening.

2. The device according to claim 1, further comprising a flashback lumen extending through the proximal portion to a fluid entry opening formed distally of the distal end of the proximal portion.

3. The device according to claim 2, wherein the fluid entry opening is formed in the connecting member.

4. The device according to claim 1, further comprising a first needle, wherein the distal lumen is sized so that, when the first needle is inserted distally thereinto, a proximal end of the first needle is inside the distal lumen distal of the needle receiving opening.

5. The device according to claim 4, further comprising a second needle, wherein the distal lumen is sized so that, when the first and second needles are inserted distally thereinto, the proximal end of the first needle and a proximal end of the second needle are inside the distal lumen distal of the needle receiving opening.

6. The device according to claim 1, wherein a minimum cross-sectional area of the connecting member is at least as great as a maximum cross-sectional area of the distal portion.

7. The device according to claim 6, wherein the minimum cross-sectional area of the connecting member is substantially equal to the maximum cross-sectional area of the distal portion.

8. The device according to claim 6, wherein the connecting member and the distal portion are substantially tubular.

9. The device according to claim 6, wherein a minimum cross-sectional area of the proximal portion is at least as great as the minimum cross-sectional area of the connecting member.

10. The device according to claim 1, wherein a cross-sectional area of the needle insertion lumen is smaller than a cross-sectional area of the distal lumen.

11. The device according to claim 1, wherein the needle insertion lumen and the needle insertion and needle receiving openings extend along a common axis.

12. The device according to claim 11, wherein the proximal portion and the connecting member are formed of a substantially rigid material.

13. The device according to claim 12, wherein the distal portion includes a rigid proximal end with a flexible tube extending distally therefrom.

14. The device according to claim 13, wherein the proximal portion, the connecting member and the proximal end of the distal portion are integrally formed.

15. The device according to claim 1, further comprising a needle pushing member which receives in a distal end thereof a proximal end of a needle, the needle pushing member being sized to fit in the needle insertion lumen.

16. The device according to claim 1, further comprising a valve in the distal lumen, wherein the valve substantially prevents the flow of blood through the distal lumen, and allows a guide wire to be pushed through the distal lumen.

17. The device according to claim 16, wherein the valve comprises a slitted diaphragm in the distal lumen.

18. The device according to claim 1, wherein the connecting member has a substantially oval cross section.

19. The device according to claim 1, wherein the connecting member includes a raised ridge located on a proximal half of the connecting member.

20. The device according to claim 1, wherein the connecting member includes an expandable member to press against a wall of the anatomical structure when the expandable member is expanded.

21. A method for sealing a puncture in an anatomical structure comprising the steps of:

inserting a proximal end of a guide wire into a distal opening of a distal lumen running through a distal portion of a device, the device including a needle receiving opening at a proximal end of the distal lumen and a needle insertion opening separated from the needle receiving opening by a tissue receiving gap;

inserting the device into the puncture along the guide wire;

removing the guide wire from the puncture and the distal lumen;

positioning the device so that the needle exit opening is located on a proximal side of the anatomical structure and the needle entry opening is located on a distal side of the anatomical structure with a first portion of the anatomical structure received within the tissue receiving gap;

inserting a first needle coupled to a first portion of suture distally through the device to exit the device via the needle insertion opening, penetrate the first portion of the anatomical structure and reenter the device via the needle receiving opening of the distal lumen;

rotating the device so that a second portion of the anatomical structure is located within the tissue receiving gap between the needle insertion opening and needle receiving opening;

inserting a second needle coupled to a second portion of suture distally through the device to exit the device via the needle insertion opening, penetrate the second portion of the anatomical structure and re-enter the device via the needle receiving opening;

withdrawing the device from the anatomical structure; and tightening the first and second portions of suture to draw the sides of the puncture together.

22. The method according to claim 21, wherein the first and second portions of suture form a single continuous length of suture.

23. The method according to claim 21, wherein the puncture is formed in a blood vessel.

24. The method according to claim 23, wherein the step of positioning the device is performed by observing the flow of blood through a flashback lumen extending through the device.

25. The method according to claim 21, wherein the steps of inserting the first and second needles into the needle insertion lumen are performed so that, when the first and second needles are inserted into the needle insertion lumen, proximal ends of the each of the first and second needles are completely received within the needle insertion lumen.

26. The method according to claim 25, wherein the first and second needles are inserted using a needle pushing member.

27. The method according to claim 21, wherein a minimum cross-sectional area of a connecting member of the device extending from a proximal to a distal side of the tissue receiving gap is at least as great as a maximum cross-sectional area of a distal portion of the device extending distally from the tissue receiving gap.

28. The method according to claim 21, wherein the step of positioning the device further includes expanding an expandable member within the puncture to position the portion of the anatomical structure within the tissue receiving gap.

* * * * *